United States Patent

Edwards

[11] Patent Number: 5,814,033
[45] Date of Patent: Sep. 29, 1998

[54] OSTOMY COUPLING

[75] Inventor: John Victor Edwards, Reigate, Great Britain

[73] Assignee: Salt & Son Limited, Birmingham, United Kingdom

[21] Appl. No.: 750,648

[22] PCT Filed: Jun. 9, 1995

[86] PCT No.: PCT/GB95/01352

§ 371 Date: Dec. 12, 1996

§ 102(e) Date: Dec. 12, 1996

[87] PCT Pub. No.: WO95/34258

PCT Pub. Date: Dec. 21, 1995

[30] Foreign Application Priority Data

Jun. 13, 1994 [GB] United Kingdom .................... 9411790

[51] Int. Cl.$^6$ ...................................................... A61F 5/44
[52] U.S. Cl. ........................................... 604/342; 604/338
[58] Field of Search ..................................... 604/332, 338, 604/339, 342

[56] References Cited

U.S. PATENT DOCUMENTS

| 3,331,370 | 7/1967 | Notley, Sr. ............................. 604/342 |
| 3,908,658 | 9/1975 | Marsan . | |
| 4,610,677 | 9/1986 | Mohiuddin . | |
| 5,167,651 | 12/1992 | Leise, Jr. et al. . | |

FOREIGN PATENT DOCUMENTS

| 02268 191 | 7/1987 | European Pat. Off. . |
| 274862 | 7/1988 | European Pat. Off. . |
| 611 123 | 8/1994 | European Pat. Off. . |
| 785 562 | 10/1967 | United Kingdom . |
| 1 217 406 | 12/1970 | United Kingdom . |
| 2115288 | 9/1982 | United Kingdom . |
| 2177924 | 2/1987 | United Kingdom . |
| WO85 03427 | 8/1985 | WIPO . |

Primary Examiner—Robert A. Clarke
Attorney, Agent, or Firm—Pepper Hamilton LLP

[57] ABSTRACT

An ostomy coupling includes two rings which can be interengaged concentrically. The inner ring (1a) has a peripheral flange (2) at one end for attachment to an abdominal pad (3a) and a radially outwardly directed peripheral bead (6) at its other end; while the outer ring (1b) has a radially outwardly directed flange (7) for attachment to an ostomy pouch (8a), and a lip (11) which engages behind the peripheral bead (6) on the inner ring in order to secure the two rings of the coupling together. The flange (7) on the outer coupling ring includes a stiffening member (10) which is disposed so as to restrain the outer coupling ring from expanding away from the inner coupling ring when the two parts of the coupling are interengaged in use.

8 Claims, 2 Drawing Sheets

OSTOMY COUPLING

RELATED APPLICATIONS

This application claims priority to International Application Number PCT/GB95/0135, filed Jun. 9, 1995.

FIELD OF THE INVENTION

This invention relates to an ostomy coupling for connecting an ostomy pouch to a pad which is adhesively attached to the abdominal skin of a user such that it surrounds the stoma.

BACKGROUND OF THE RELATED ART

Ostomy couplings generally include two rings which can be interengaged concentrically, the inner ring having means at one end for attachment to an abdominal pad and a radially outwardly directed peripheral bead at its other end, whilst the outer ring has a radially outwardly directed flange for attachment to an ostomy pouch and is adapted to fit over the inner ring with a lip on the outer ring engaged behind the peripheral bead on the inner ring in order to secure the two components of the coupling together. An ostomy coupling of this type is disclosed, for example, in GB 1217406.

Whilst such couplings are satisfactory in many respects, there is a tendency for the outer coupling ring attached to the pouch to expand away from the inner body-side coupling during use, as pressure builds up within the pouch causing the pouch to spread out. This in turn may cause leakage of gas from the pouch which is obviously undesirable and unpleasant for the user.

WO-A-8503427 discloses a coupling of the aforementioned kind provided with a belt attaching ring mounted on the outer coupling ring, the belt attaching ring receiving the ends of a belt fitted around the waist of a user to assist in retaining the ostomy pouch in position. The belt attaching ring may also slide axially to a position in which it assists in clamping the lip in its engaged position behind the peripheral bead on the inner coupling ring. However, such an arrangement is only effective when used with a waist belt attached to the belt ring.

SUMMARY OF THE INVENTION

It is an object of the present invention to alleviate the problem of leakage of gas from the pouch which does not depend on the provision of a belt attaching ring and waist belt.

According to the invention, the flange on the outer coupling ring includes a stiffening member made of a material stiffer than that forming the outer coupling ring and disposed in a recess formed in the outwardly directed flange of the outer ring, said recess being open at the opposite surface to the surface attached to the pouch whereby said stiffening member acts to restrain the outer coupling ring from expanding away from the inner coupling ring when the two parts of the coupling ring are engaged in use.

In one embodiment, the flange is of channel cross-section with the stiffening member located in the channel. The stiffening member may be secured in position by any suitable means of an adhesive, by heat sealing or making it a snap fit in the recess or channel.

The radially outer surface of the inner ring and the radially inner surface of the lip on the outer ring may be tapered in a complementary fashion such as to assist the outer ring being fitted over the inner ring. The lip on the outer ring may be wedge-shaped in cross section, with the narrower end of the wedge attached to the flange by a web or neck portion.

BRIEF DESCRIPTION OF THE DRAWINGS

The invention will now be further described, by way of example, with reference to the accompanying drawings, in which.

DESCRIPTION OF BEST MODES OF THE INVENTION

Figure 1:
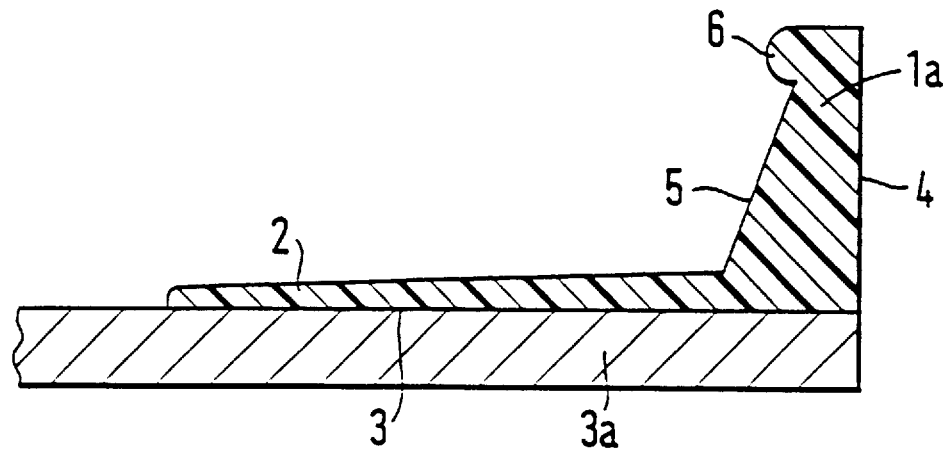
FIG. 1 shows a cross-section through part of an inner coupling ring according to one embodiment of the invention.
Figure 4:
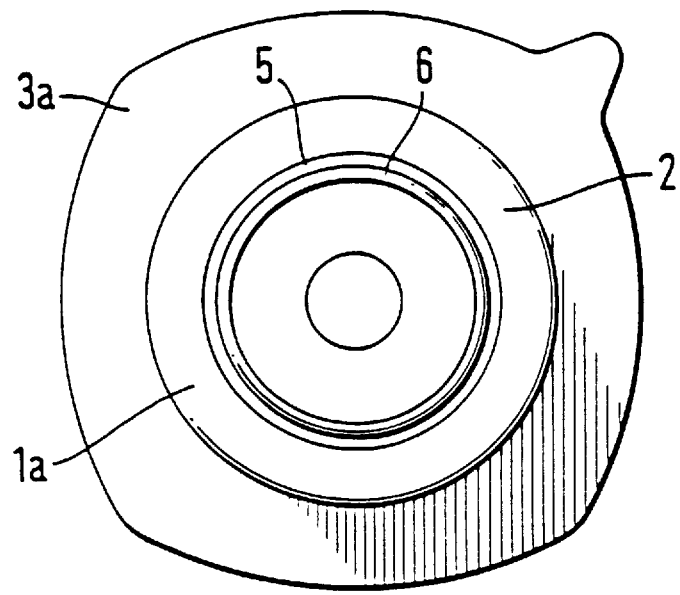
FIG. 4 is a plan view of an abdominal pad having the inner coupling ring shown in FIG. 1.

Referring to FIGS. 1 and 4, the inner ring 1a of an ostomy coupling has an outwardly directed peripheral flange 2 at one end, with an attachment surface 3 for attaching the inner ring about the aperture in an abdominal pad 3a of a type known in the art. The ring has a cylindrical radially inner surface 4 and a frusto-conical or tapered radially outer surface 5. At the opposite end of the ring from the flange 2 is a peripheral bead 6 having a generally semicircular cross-section.

Figure 2:
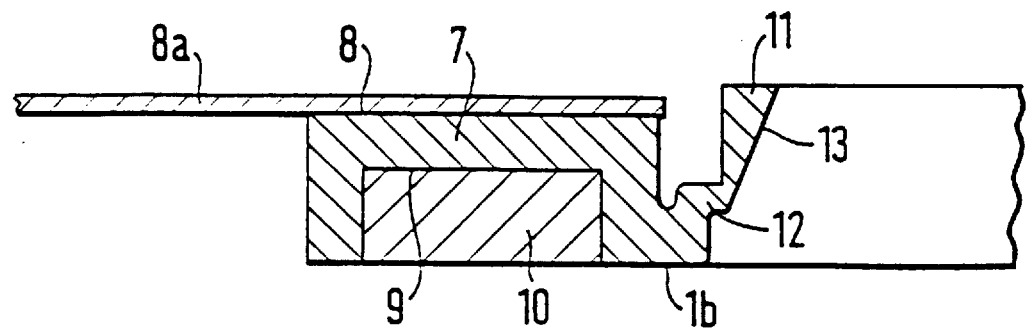
FIG. 2 shows a cross-section through part of an outer coupling ring intended to engage with the inner ring shown in FIG. 1.
Figure 3:
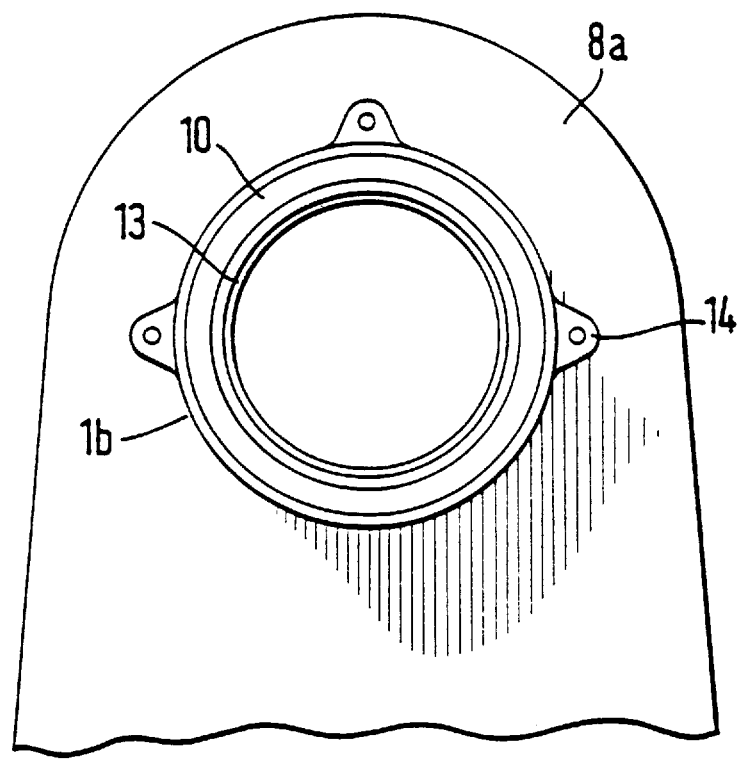
FIG. 3 is a plan view of an ostomy pouch having the outer coupling ring shown in FIG. 2.

FIGS. 2 and 3 show the outer coupling ring 1b which forms the other element of the coupling. The ring comprises a flange 7 which has an attachment surface 8 for attaching about the aperture in an ostomy pouch 8a of a type known in the art. The flange 7 is of generally channel cross-section to provide a rectangular recess 9 within which is secured an annular stiffening member 10 of corresponding rectangular cross-section.

Attached to the radially inner side of the flange 7 is a lip 11 of wedge shaped cross-section, extending from an angled neck 12 on said radially inner side of the flange 7. The lip 11 has a frusto-conical or tapered surface 13 on its radially inner side, the slope of which conforms to that of the conical surface 5 of the inner ring 1a.

To assemble the coupling, the outer ring 1b is placed over the inner ring 1a and pushed towards the latter until the lip 11 is deflected as it passes over the peripheral bead 6 and then latches behind the bead, the conical surfaces 5, 13 coming into contact to seal the coupling.

The outer ring is preferably made of ethylene vinyl acetate, the stiffening member 10 of nylon 66 or rigid polyvinyl chloride and the inner ring of low density polyethylene. In another example, the outer ring is made of 15% ethylene vinyl acetate and, 85% low density polyethylene. However, those skilled in the art may select alternative suitable materials, as long as the stiffening member is made of a material more rigid than that of the outer ring 1b.

When the coupling is assembled, the stiffening member 10 lies substantially adjacent and parallel to the flange 2 of the inner ring. The relative rigidity of the stiffening member serves to restrain the outer ring from expanding away from the inner ring even if the ostomy pouch inflates and expands. Thus, any tendency for leakage is greatly reduced.

One or more pull tabs 14, shown in FIG. 3, may be provided on the outer ring 7 as is known in the art to facilitate its removal from the inner ring 1.

The invention, as exemplified by the described embodiment, thus provides an ostomy coupling which is easily assembled and disassembled yet is not prone to leaks. The coupling is also of low profile, easy to couple together and largely self-aligning due to its tapered configuration which is of particular advantage to the poorly sighted. Moreover the smooth inner surface 4 of the inner ring makes it easy to keep clean.

If desired, the stiffening member 10 may be made in various grades of stiffness, thus providing a different degree of security depending on the stiffness chosen. Such stiffening members could be colour coded or otherwise identified according to the degree of stiffness which they impart.

Such a facility enables the degree of security to be related to the activity of the wearer. For example, a large sedentary user may be content with a coupling incorporating a lower degree of stiffness and hence greater ease of uncoupling, whereas a more active user may require a greater degree of security and hence use a coupling incorporating a higher degree of stiffness but which requires greater force to separate the two coupling members.

I claim:

1. An ostomy coupling comprising two rings which can be interengaged concentrically, the inner ring (1a) having a flange (2) at one end for attachment to an abdominal pad and a radially outwardly directed peripheral bead (6) at its other end, and the outer ring (1b) having a radially outwardly directed flange (7) for attachment to an ostomy pouch and a lip (11) which engages behind the peripheral bead (6) on the inner ring in order to secure the two rings of the coupling together, characterised in that the flange on the outer coupling ring (1b) includes a stiffening member (10) made of a material stiffer than that forming the outer coupling ring and disposed in a recess (9) formed in said flange of said outer ring (1b), said recess being open at the opposite surface to the surface attached to the pouch, whereby said stiffening member acts to restrain the outer coupling ring from expanding away from the inner coupling ring when the two parts of the coupling are interengaged in use.

2. An ostomy coupling as claimed in claim 1, characterised in that said flange (7) is of channel section with the stiffening member (10) located in the channel.

3. An ostomy coupling as claimed in claim 1, characterised in that the stiffening member (10) is secured in position by means of an adhesive or heat sealing.

4. An ostomy coupling as claimed in claim 1, characterised in that the stiffening member (10) is a snap fit in the recess or channel (9).

5. An ostomy coupling as claimed in claim 1, characterised in that the radially outer surface (5) of the inner ring (1a) and the radially inner surface (13) of the lip on the outer ring (1b) are tapered in a complementary fashion.

6. An ostomy coupling as claimed in claim 1, characterised in that the lip (11) on said outer ring (1b) is wedge-shaped in cross-section, with the narrower end of the wedge attached to the flange (7) by a neck or web portion (12).

7. An ostomy coupling as claimed in claim 1, characterised in that the stiffening member (10) is made in various grades of stiffness each of which bears an identification to indicate the degree of stiffness which it imparts, thereby enabling a choice of stiffening member to be fitted to the outer coupling ring (1b).

8. An ostomy coupling as claimed in claim 1, characterised in that the outer ring (1b) is made at least partially of ethylene vinyl acetate, the stiffening member is made of nylon or rigid PVC and the inner ring is made of low density polyethylene.

* * * * *